(12) United States Patent
Lee et al.

(10) Patent No.: US 8,106,941 B2
(45) Date of Patent: Jan. 31, 2012

(54) STEREOSCOPIC DISPLAY APPARATUS

(75) Inventors: Shih Tseng Lee, Taipei (TW);
Chieh-Tsai Wu, Taipei County (TW);
Wen-Chung Teng, Taipei County (TW);
Hsin-Liang Chen, Taipei (TW)

(73) Assignee: Chang—Gung University, Tao-Yuan (TW)

( * ) Notice: Subject to any disclaimer, the term of this patent is extended or adjusted under 35 U.S.C. 154(b) by 900 days.

(21) Appl. No.: 12/157,789

(22) Filed: Jun. 13, 2008

(65) Prior Publication Data

US 2009/0135248 A1    May 28, 2009

(30) Foreign Application Priority Data

Nov. 22, 2007 (TW) ................................ 96144346 A

(51) Int. Cl.
*H04N 7/18* (2006.01)
*G06F 15/16* (2006.01)

(52) U.S. Cl. ........................................................ 348/51

(58) Field of Classification Search ............... 348/51–56
See application file for complete search history.

(56) References Cited

U.S. PATENT DOCUMENTS

| | | | | |
|---|---|---|---|---|
| 4,561,731 A | * | 12/1985 | Kley | 349/1 |
| 5,506,705 A | * | 4/1996 | Yamamoto et al. | 349/13 |
| 5,991,085 A | * | 11/1999 | Rallison et al. | 359/630 |
| 6,407,724 B2 | * | 6/2002 | Waldern et al. | 345/8 |
| 7,016,116 B2 | * | 3/2006 | Dolgoff | 359/630 |
| 7,492,523 B2 | * | 2/2009 | Dolgoff | 359/630 |
| 2001/0055152 A1 | * | 12/2001 | Richards | 359/462 |
| 2002/0034004 A1 | * | 3/2002 | Khoshnevis et al. | 359/407 |
| 2002/0186348 A1 | * | 12/2002 | Covannon et al. | 351/240 |
| 2003/0035085 A1 | | 2/2003 | Westort et al. | |
| 2007/0223090 A1 | * | 9/2007 | Dolgoff | 359/478 |
| 2008/0143965 A1 | * | 6/2008 | Cowan et al. | 353/8 |

FOREIGN PATENT DOCUMENTS

| TW | 520772 U | 2/2003 |
|---|---|---|
| TW | 200409942 A | 6/2004 |
| TW | 200409943 A | 6/2004 |

* cited by examiner

*Primary Examiner* — Zarni Maung
(74) *Attorney, Agent, or Firm* — Hudak, Shunk & Farine Co. LPA

(57) ABSTRACT

The present invention discloses a stereoscopic display apparatus comprising a first and a second image displayer, an aspherical reflection mirror, a beamsplitter and a housing. The first and the second image displayer are used for projecting a first and a second image light respectively. The aspherical reflection mirror is used for refracting the image light and for changing a polarity of the image light. The beamsplitter, disposed between the image generator and the aspherical reflection mirror, is used for deflecting a proceeding route of the image light based on the polarity of the optical signal. The housing has at least one opening for an operator to inspect a first image and a second image through.

18 Claims, 7 Drawing Sheets

US 8,106,941 B2

STEREOSCOPIC DISPLAY APPARATUS

FIELD OF THE INVENTION

The present invention relates to a stereoscopic display apparatus, and more particularly to the stereoscopic display apparatus that is capable of being worn on operators, therefore, it can replace the traditional flat panel display with the advantages of resolution enhancement, appropriate panel size and providing the best suitable conditions for operators to use.

BACKGROUND OF THE INVENTION

Since the technology in medical treatment has been advanced nowadays, it is still sometimes happened a mistaken determination of a patient's internal condition by reading the x-ray pictures due to the differences between the object body and its two-dimension image. Besides, if the patient lives in outlying districts, it may need other support from remote medical institution. In this case, doctor at remote end can not directly contact to the patients and may only verify their situation by limited image information, and it is more possibility for doctor to determine erroneously. Currently, the stereoscopic display apparatus has applied to help the doctor to determine patient's internal condition for improving the precision. However, the traditional stereoscopic display apparatus is normally set in the hospital because of its big size, therefore, it is not capable of being portable use for doctors, and decreases its convenience.

In view of the drawbacks of the prior art, the inventor of the present invention based on years of experience to conduct extensive researches and experiments, and finally developed a stereoscopic display apparatus to overcome the drawbacks of the prior art.

SUMMARY OF THE INVENTION

Accordingly, the object of the present invention is to provide a stereoscopic display apparatus to improve its using convenience.

To achieve the foregoing object, the present invention provides a stereoscopic display apparatus comprising a first image displayer, a second image displayer, an aspherical reflection mirror, a beamsplitter, an opaque plate and a housing. The first image displayer is used for projecting a first image light. The second image displayer is used for projecting a second image light. The aspherical reflection mirror is used for refracting the first image light and the second image light, and for changing a polarity of the first image light and the second image light. The beamsplitter is disposed between the aspherical reflection mirror, the first image displayer and the second image displayer, and used for deflecting a proceeding route of the first image light and the second image light based on the polarity of the first image light and the second image light respectively. The opaque plate is used for projecting the first image light and the second image light to form a first image and a second image thereon. The housing is used for containing the first image displayer, the second image displayer, the aspherical reflection mirror, the beamsplitter and the opaque plate. The housing has at least one opening for an operator to inspect the first image and the second image through.

Preferably, the housing further has a first opening and at least one second opening. Therefore, the refraction light of first image light and the refraction light of second image light can process through the first opening, and then project on an external object body to generate a first image and a second image. The second opening is used for an operator to inspect the first image and the second image through.

To make our examiner to understand the technical characteristics and effects of the present invention, we use preferred embodiments with related drawings for the detail description of the present invention.

BRIEF DESCRIPTION OF THE DRAWINGS

The subject matter regarded as the invention is particularly pointed out and distinctly claimed in the concluding portion of the specification. The invention together with features and advantages thereof may best be understood by reference to the following detailed description with the accompanying drawings in which:

The subject matter regarded as the invention is particularly pointed out and distinctly claimed in the concluding portion of the specification. The invention together with features and advantages thereof may best be understood by reference to the following detailed description with the accompanying drawings in which:

DETAILED DESCRIPTION OF THE PREFERRED EMBODIMENTS

The forgoing and other objects, features and advantages of the present invention will be better understood from the following detailed description taken with the accompanying drawing, and the same referring numerals are used for the same components in accordance with the present invention.

Figure 1A:
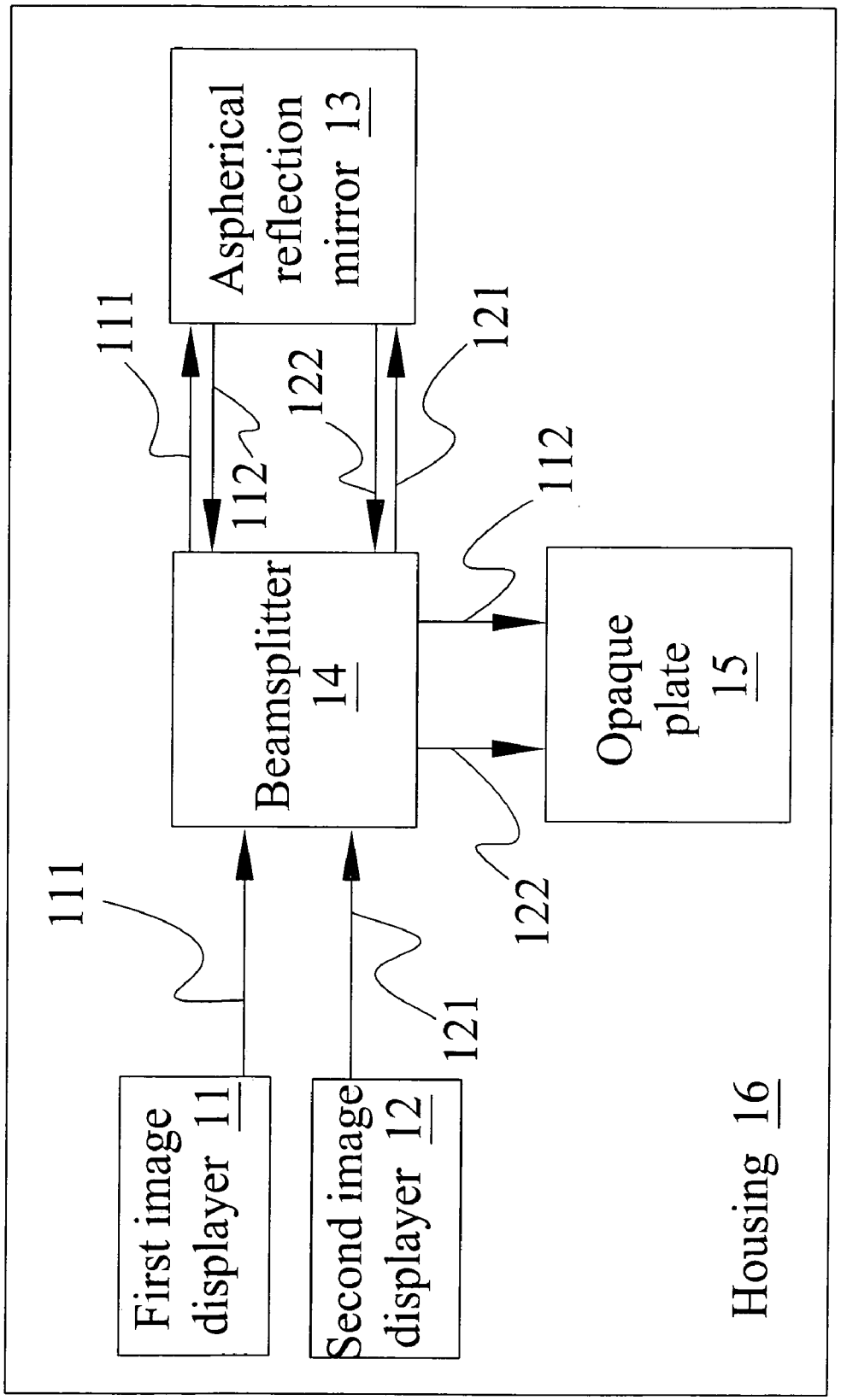
FIG. 1A is a schematic block diagram of a stereoscopic display apparatus in accordance with a first preferred embodiment of the present invention.

FIG. 1A illustrates a schematic block diagram of a stereoscopic display apparatus in accordance with a first preferred embodiment of the present invention. The stereoscopic display apparatus comprises a first image displayer 11, a second image displayer 12, an aspherical reflection mirror 13, a beamsplitter 14, an opaque plate 15 and a housing 16. The first image displayer 11 and the second image displayer 12 are electrically connected to a multimedia apparatus for receiving an electrical signal of the first image and the second image. The first image displayer 11 and the second image displayer 12 are used for converting the electrical signal of the first image and the second image into the first image light 111 and the second image light 121 and projecting it afterward.

The aspherical reflection mirror 13 is used for refracting the first image light 111 and the second image light 121, and changing the polarity of the first image light 111 and the second image light 121. For easier observation, the first image light and the second image light after being reflected are marked by 121 and 122. The polarity of the first image light 111 and the second image light 121 are different from the polarity of first image light 112 and the second image light 122. The polarity means the light traveling-wave phase. The beamsplitter 14 is disposed between the first image displayer 11, the second image displayer 12 and the aspherical reflection mirror 13, and used for deflecting the processing path of the first image light and the second image light based on the their polarity respectively.

When being emitted from the first image displayer 11 and the second image displayer 12 into the beamsplitter 14, the first image light 111 and the second image light 121 transmit through the beamsplitter 14. However, after the first image light 111 and the second image light 121 are refracted from he aspherical reflection mirror 13, polarity of the first image light 112 and the second image light 122 are changed and then refracted by the beamsplitter 14 due to their polarity. The opaque plate 15 is used for projecting the first image light 112 and the second image light 122 to form a first image and a second image thereon. The housing 16 is used for containing the first image displayer 11, the second image displayer 12, the aspherical reflection mirror 13, the beamsplitter 14 and the opaque plate 15. The housing 16 has at least one opening for an operator to inspect the first image and the second image through.

Preferably, the multimedia apparatus can be a computer. The aspherical reflection mirror 13 is preferably an aspherical mirror to increase the light sensitivity and distortion correction capability of the first image light and the second image light. The beamsplitter 14 is preferably a multilayer coating beamsplitter with 50% of transmittance rate and 50% of refraction rate, which can be used as to reduce the specular reflection, increase the translucence and change the polarity of a light wave.

Besides, the housing 16 can contain a control module, if necessary, for controlling the first image displayer 11 and the second image displayer 12. The opening of the housing 16 can be installed with an anti-glare goggles thereupon for operators to eliminate the interference when viewing the first image and second image. Preferably, the first image and the second image can be a left-eye image and right-eye image which can form a stereoscopic image. The opaque plate 15 can either be part of the housing 16 or be a PVC plastic hardcover.

Figure 1B:
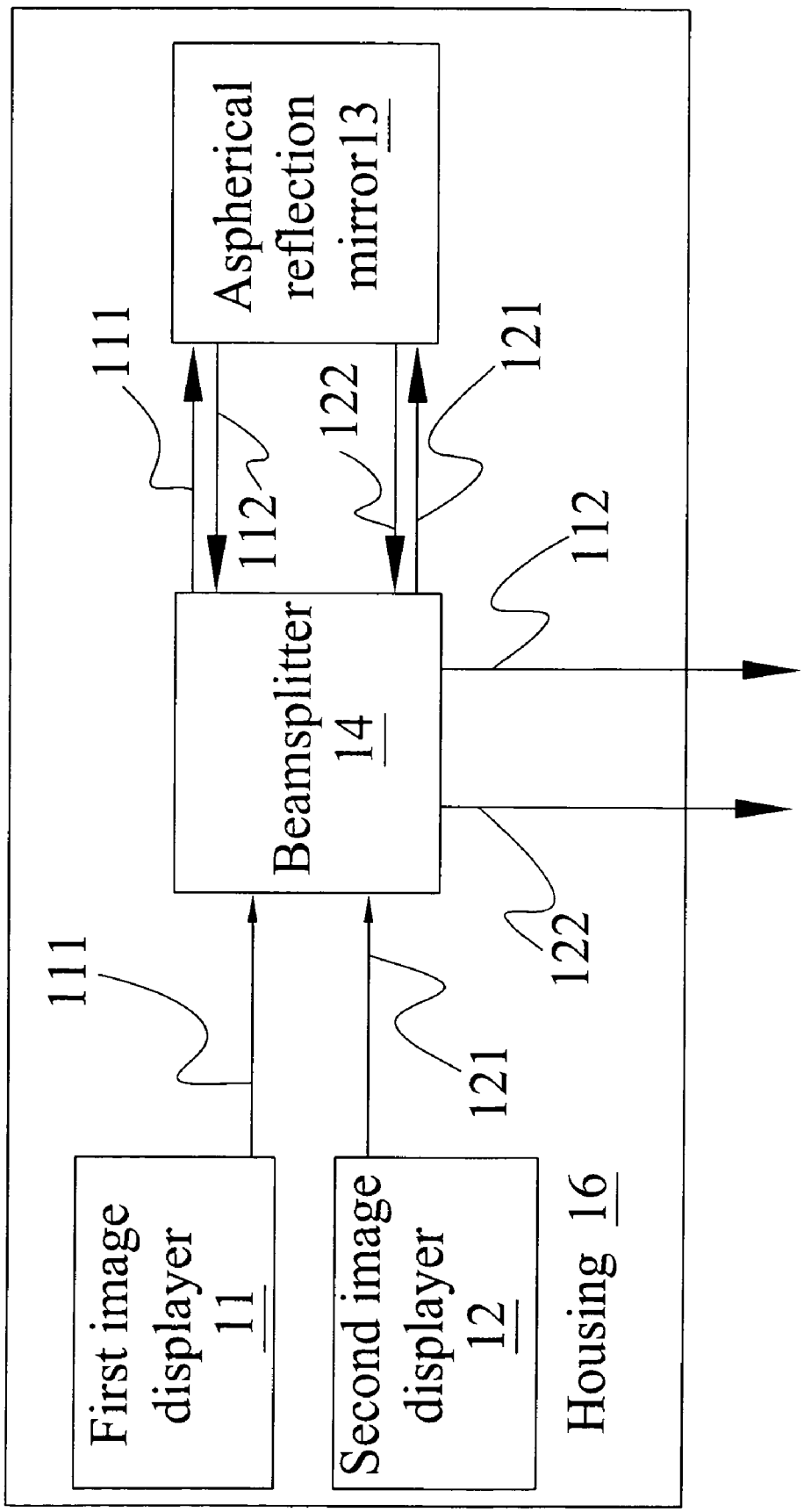
FIG. 1B is a schematic block diagram of a stereoscopic display apparatus in accordance with a second preferred embodiment of the present invention.

Please referring to FIG. 1B for a schematic block diagram of a stereoscopic display apparatus in accordance with a second preferred embodiment of the present invention, the stereoscopic display apparatus comprises a first image displayer 11, a second image displayer 12, an aspherical reflection mirror 13, a beamsplitter 14 and a housing 16. The first image displayer 11 and the second image displayer 12 electrically connect to a multimedia apparatus for receiving an electrical signal of the first image and the second image. The first image displayer 11 and the second image displayer 12 are used for converting the electrical signal of the first image and the second image into the first image light 111 and the second image light 121.

The aspherical reflection mirror 13 is used for refracting the first image light 111 and the second image light 121, and changing the polarity of the first image light 111 and the second image light 121. For easier observation, the first image light and the second image light after being reflected are marked by 121 and 122. The polarity of the first image light 111 and the second image light 121 are different from the polarity of first image light 112 and the second image light 122. The beamsplitter 14 is disposed between the first image displayer 11, the second image displayer 12 and the aspherical reflection mirror 13, and used for deflecting the processing path of the first image light and the second image light based on the their polarity respectively.

The housing 16 is used to contain the first image displayer 11, the second image displayer 12, the aspherical reflection mirror 13 and the beamsplitter 14. The housing 16 has a first opening and at least one second opening. The refracted light 112 of first image light 111 and said refracted light 122 of second image light 121 can pass through the first opening and then form a first image and a second image on external object body. The second opening is used for an operator to inspect the first image and the second image through.

Besides, the housing 16 can contain a control module, if necessary, for controlling the first image displayer 11 and the second image displayer 12. The opening of the housing 16 can be installed with an anti-glare goggles thereupon for operators to eliminate the interference when viewing the first image and second image. Preferably, the first image and the second image can be a left-eye image and a right-eye image which can be overlaid to form a stereoscopic image.

Figure 2:
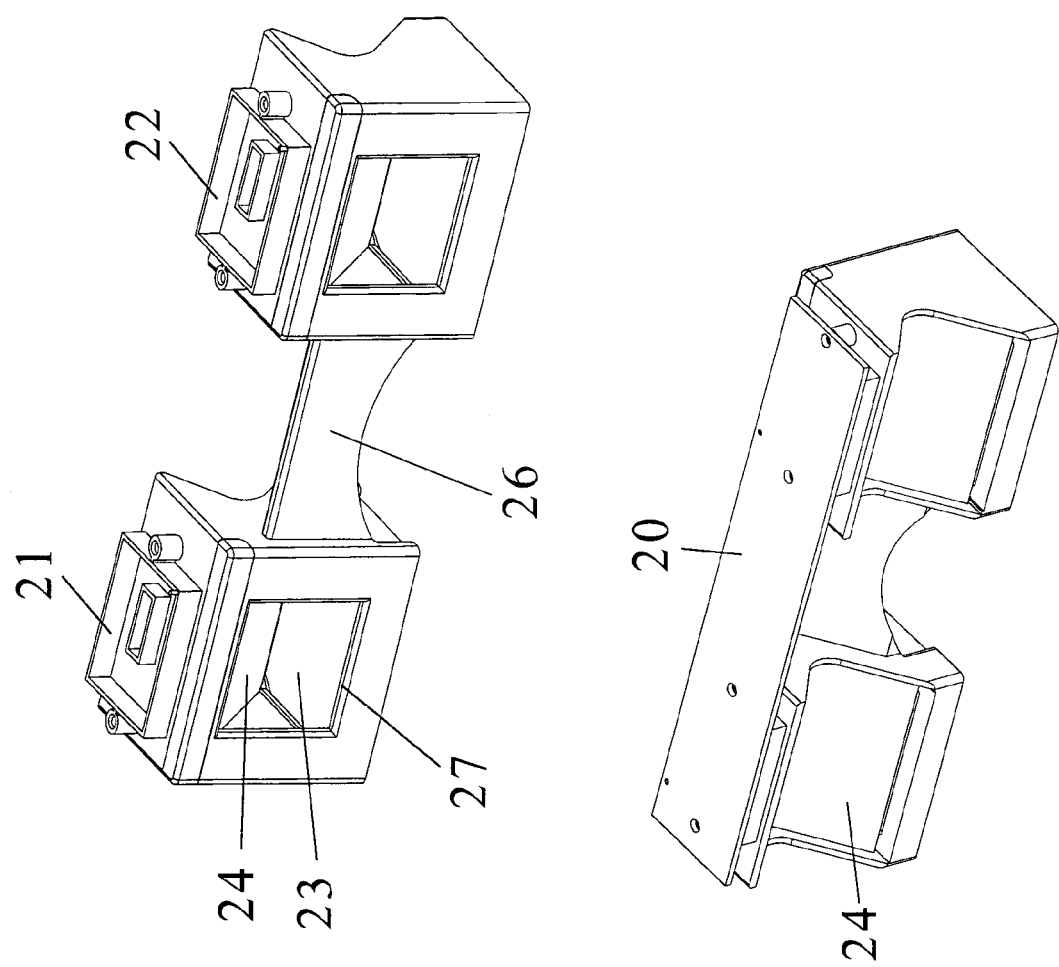
FIG. 2 is a stereo view of a stereoscopic display apparatus in accordance with a preferred embodiment of the present invention.
Figure 3A:
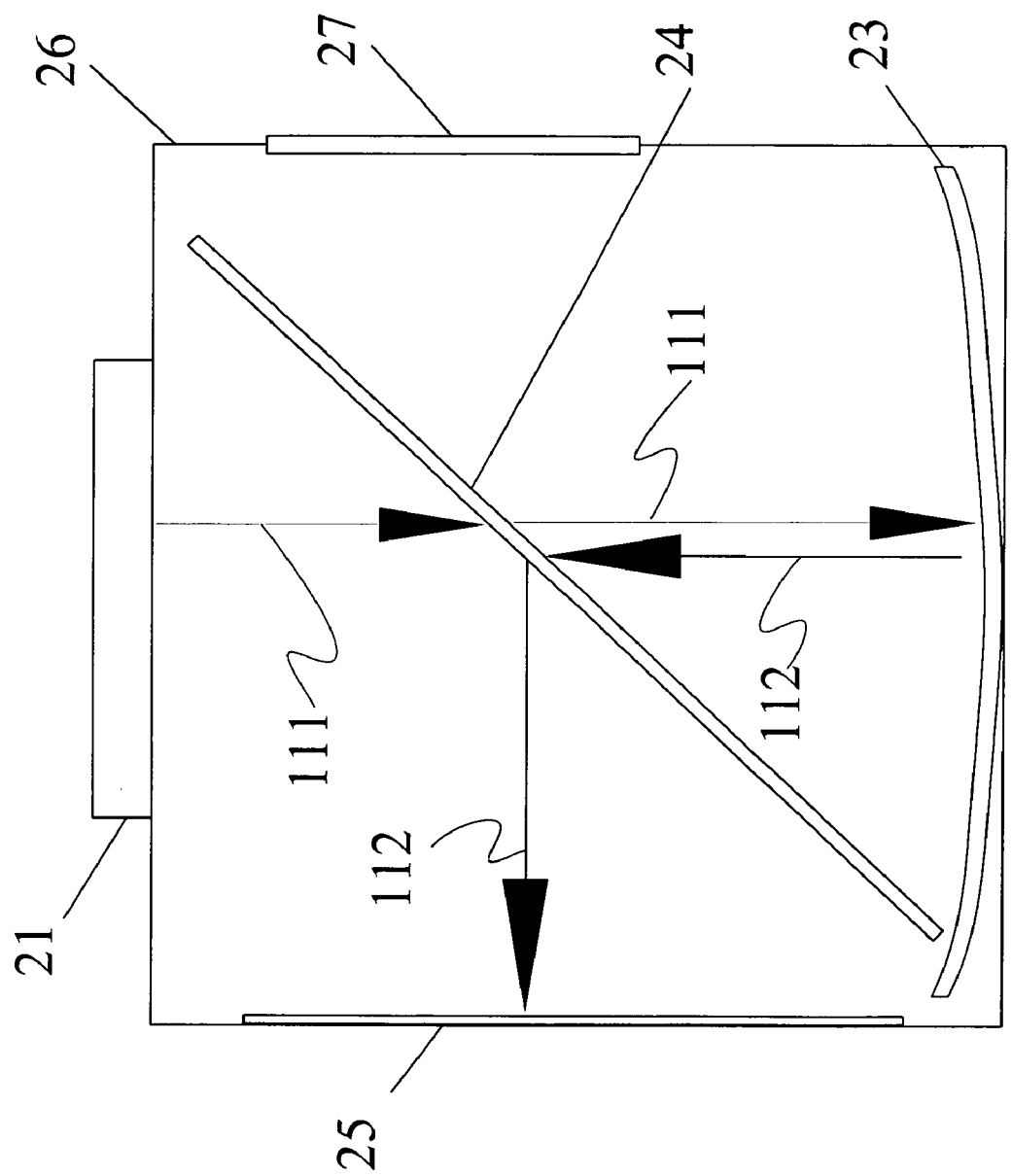
FIG. 3A is a side elevation view of a stereoscopic display apparatus in accordance with a first preferred embodiment of the present invention.
Figure 3B:
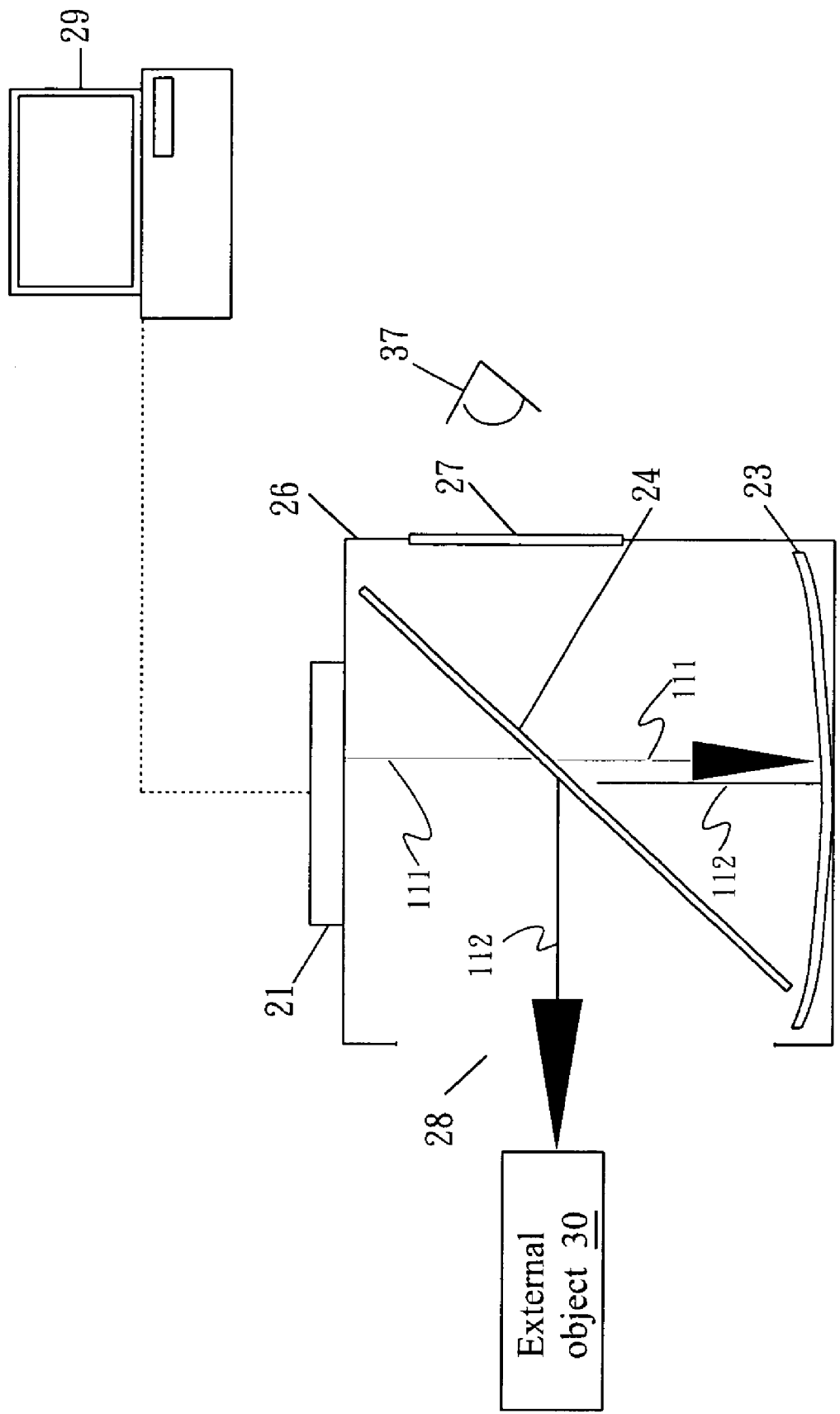
FIG. 3B a side elevation view of a stereoscopic display apparatus in accordance with a second preferred embodiment of the present invention.

FIG. 2, FIG. 3A, and FIG. 3B illustrate a stereo view of a stereoscopic display apparatus, a side elevation view of a first preferred embodiment and a side elevation view of a second preferred embodiment respectively. The same referring numerals are used for the same components in accordance with the present invention. The stereoscopic display apparatus comprises a control module 20, a first image displayer 21, a second image displayer 22, an aspherical reflection mirror 23, a multilayer coating beamsplitter 24, a PVC plastic hardcover 25, a housing 26, an opening of anti-glare goggles 27 and a first opening 28.

The control module 20 is used for controlling the first image displayer 21 and the second image displayer 22. The multilayer coating beamsplitter 24 is disposed between the first image displayer 21, said second image displayer 22 and said aspherical reflection mirror 23. The first image displayer 21 and the second image displayer 22 are used for receiving an electrical signal of the left-eye image and right-eye image respectively, then converting the electrical signal of the left-eye image and right-eye image into corresponding image light, and projecting an first image light 111 and an second image light 121 to the multilayer coating beamsplitter 24. The polarity of the first image light 111 and the second image light 121 can process through the multilayer coating beamsplitter 24. Here, for the convenience, the drawing of FIG. 3A, FIG. 3B only present the proceeding route of the first image light 111 and it will be the reference for the second image light 121.

The aspherical reflection mirror 23 is used for refracting the first image light 111 and the second image light 121 which has already processed through the multilayer coating beamsplitter 24, and for changing a polarity of the first image light 112 and the second image light 122. Because the polarity has been changed, the first image light 112 and the second image light 122 can not processed through the multilayer coating beamsplitter 24 and then be projected on the PVC plastic hardcover 25.

In FIG. 3A, PVC plastic hardcover 25 can be used for projecting the first image light 112 and the second image light 122, thus forming a left-eye image and a right-eye image thereon respectively. The housing 26 is used for containing the first image displayer 21, the second image displayer 22, the aspherical reflection mirror 23, the beamsplitter 24 and the PVC plastic hardcover. Therefore, operators can inspect the stereoscopic image formed by the left-eye image and the right-eye image through at least one opening with anti-glare goggles 27 installed thereupon.

Moreover, in FIG. 3B, the first image displayer 21 and the second image displayer 22 is used for receiving an electrical signal of the left-eye image and right-eye image respectively in accordance with an external object 30 which outputted by a computer apparatus, then converting the electrical signal of the left-eye image and right-eye image into an image light, and then projecting an first image light 111 and an second image light 121 in the multilayer coating beamsplitter 24. Moreover, the refraction light of first image light 11 1 and the refraction light of second image light 121 can process through the first opening 28, and then work with an image of an external object 30 to generate a left-eye image and a right-eye image. Therefore, operators can inspect the stereoscopic image formed by left-eye image, the right-eye image and the external object 30 through at least one opening with anti-glare goggles 27 installed thereupon.

Figure 4A:
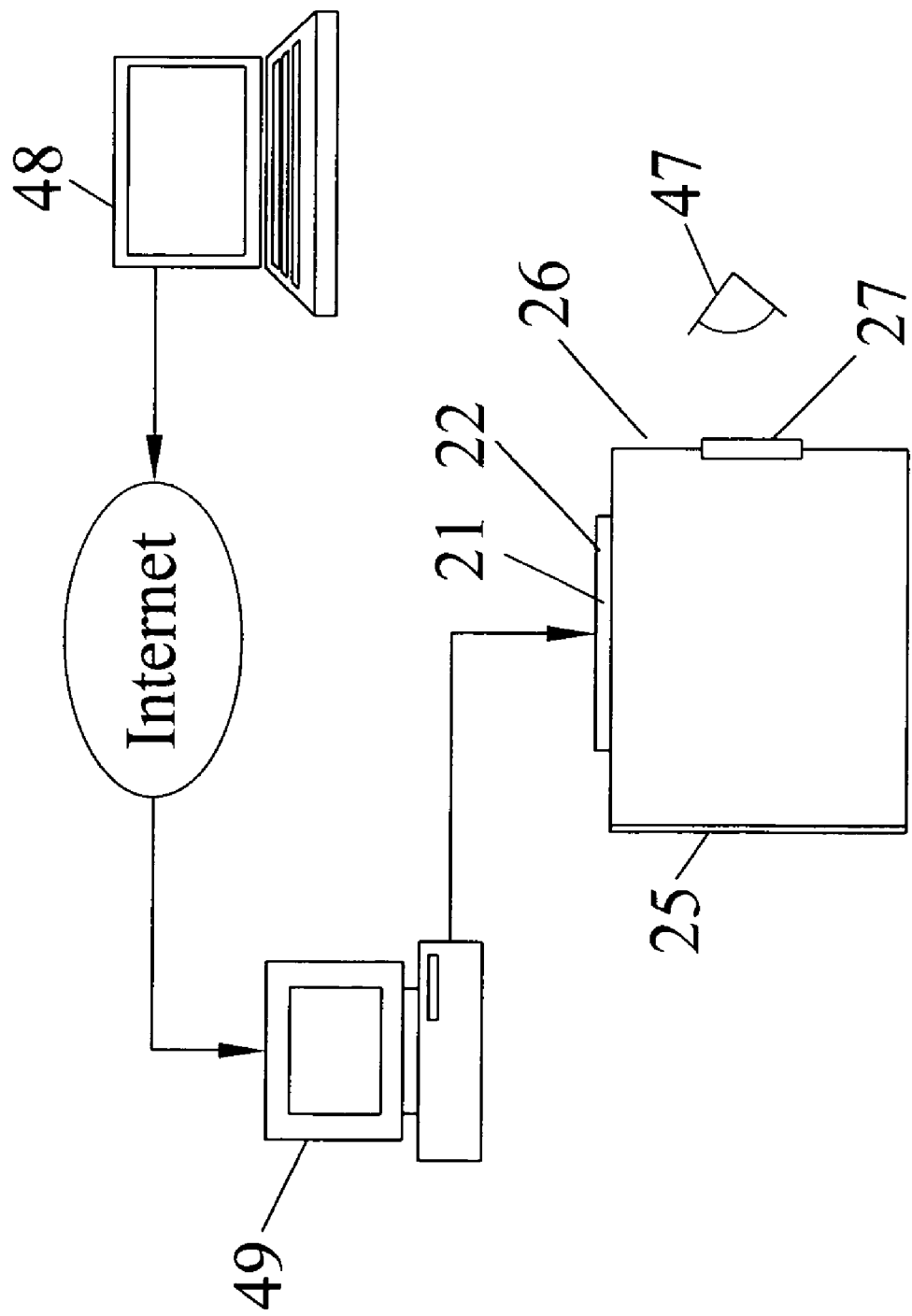
FIG. 4A is an evaluation view of a stereoscopic display apparatus applying in medical treatment in accordance with a first preferred embodiment of the present invention.

Please referring to FIG. 4A for an evaluation view of a stereoscopic display apparatus applying in remote medical institution with a first preferred embodiment of the present invention. The computer at remote medical institution 48 sent the plurality of pathology images to the local computer by Internet. The local computer 49 connects to the stereoscopic display apparatus. Doctors can use the control module 20 to operate the first image displayer 21 and the second image displayer 22, therefore to project the image light 111, 121 to the aspherical reflection mirror 23 through the multilayer coating beamsplitter 24 when receiving the pathology images from local computer 49. The aspherical reflection mirror 23 is used for refracting and amplifying the first image light 111 and the second image light 121 which has already processed through the multilayer coating beamsplitter 24, and for changing its polarity of the first image light 112 and the second image light 122. Due to the polarity of the first image light 112 and the second image light 122 has been changed, the multilayer coating beamsplitter 24 will refract the image light 112, 122 in the PVC plastic hardcover 25. Therefore, doctors can inspect the pathology images on the PVC plastic hardcover 25 through the opening 27.

Figure 4B:
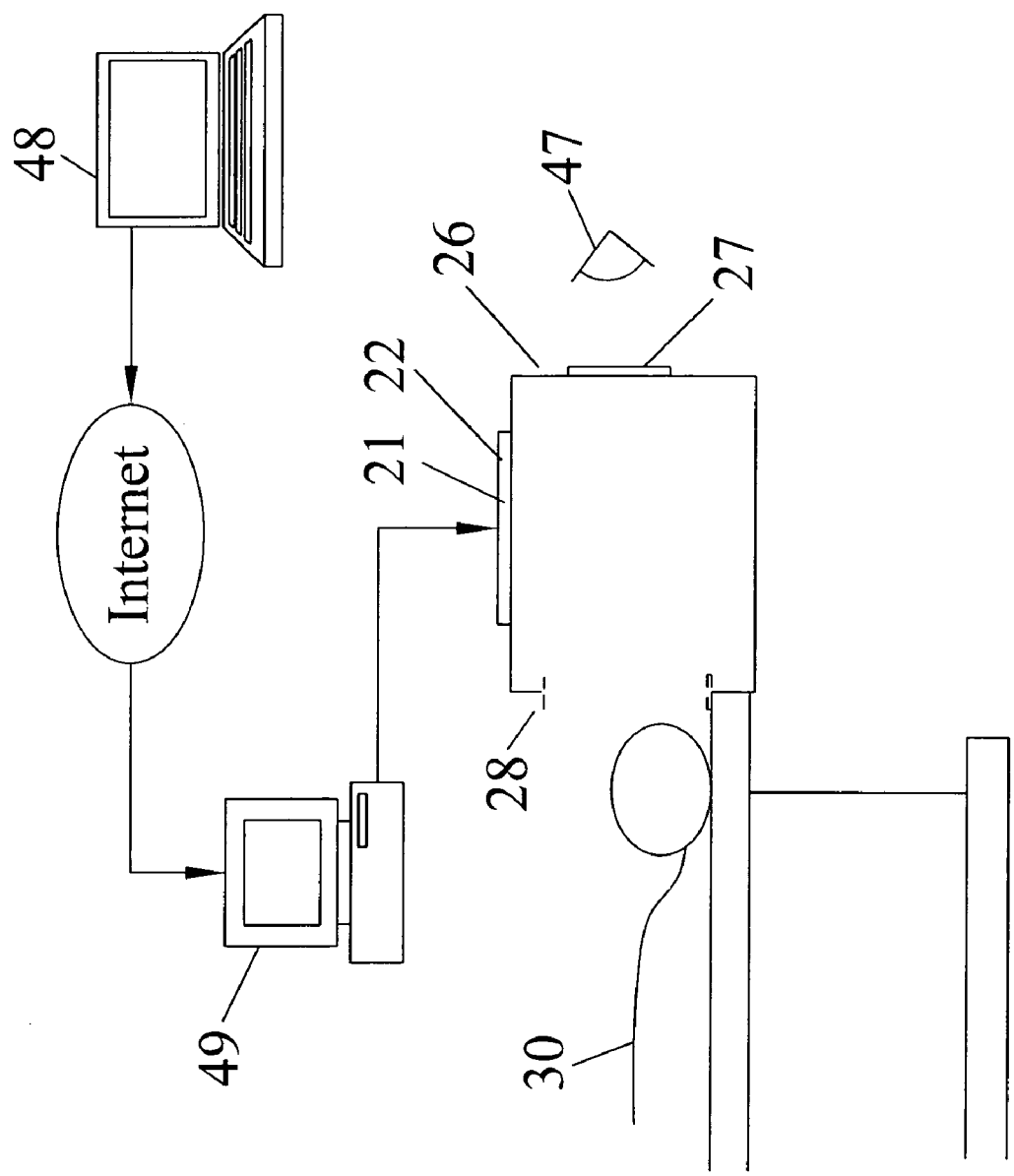
FIG. 4B is a schematic view of a stereoscopic display apparatus applying in medical treatment in accordance with a second preferred embodiment of the present invention.

Please referring to FIG. 4B for an evaluation view of a stereoscopic display apparatus applying in remote medical institution with a second preferred embodiment of the present invention. The computer at remote medical institution 48 sent the plurality of pathology images to the local computer by Internet. The local computer 49 connects to the stereoscopic display apparatus. Doctors can use the control module 20 to operate the first image displayer 21 and the second image displayer 22, therefore to project the image light 111, 121 to the aspherical reflection mirror 23 through the multilayer coating beamsplitter 24 when receiving the pathology images from local computer 49. The aspherical reflection mirror 23 is used for refracting and amplifying the first image light 111 and the second image light 121 which has already processed through the multilayer coating beamsplitter 24, and for changing its polarity of the first image light 112 and the second image light 122. Due to the polarity of the first image light 112 and the second image light 122 has been changed, the multilayer coating beamsplitter 24 will refract the image light 112, 122 to the first opening 28. Therefore, doctors can inspect the pathology images combined with the external object 30 through the opening with the anti-glare goggles 27 installed thereupon.

While the invention has been described in terms of specific embodiments of the present invention, it is not limited to such detail since numerous modifications and variations could be made thereto by those skilled in the art without departing from the scope and spirit of the present invention. Therefore, the features and advantages of the present invention will be set forth in the claims.

What is claimed is:

1. A stereoscopic display apparatus comprising:
   a first image displayer, for projecting a first image light;
   a second image displayer, for projecting a second image light;
   an aspherical reflection mirror, for refracting said first image light and said second image light, and for changing a polarity of said first image light and said second image light;
   a beamsplitter, disposed within said first image displayer, said second image displayer and said aspherical reflection mirror, for deflecting the proceeding path of said first image light and said second image light based on said polarity of said first image light and said second image light;
   an opaque plate, for projecting said first image light and said second image light, thus forming a first image and a second image thereon; and
   a housing, for containing said first image displayer, said second image displayer, said aspherical reflection mirror, said beamsplitter and said opaque plate, said housing having at least one opening for an operator to inspect said first image and said second image;
   wherein said first image displayer and said second image displayer are used for receiving an electrical signal of a left-eye image and a right-eye image respectively, and said left-eye image is said first image and said right-eye image is said second image.

2. The stereoscopic display apparatus of claim 1, wherein said first image displayer and said second image displayer are electrically connected to an multimedia apparatus for receiving an electrical signal of said first image and said second image, and said first image displayer and said second image displayer convert said electrical signal of said first image and said second image into said first image light and said second image light.

3. The stereoscopic display apparatus of claim 2, wherein said multimedia apparatus is a computer.

4. The stereoscopic display apparatus of claim 1, wherein said aspherical reflection mirror can increase the light sensitivity and distortion correction capability of said first image light and said second image light.

5. The stereoscopic display apparatus of claim 1, wherein said beamsplitter is a multilayer coating beamsplitter.

6. The stereoscopic display apparatus of claim 1, wherein said housing further contains a control module for controlling said first image displayer and said second image displayer.

7. The stereoscopic display apparatus of claim 1, further comprising an anti-glare goggles installed on said opening.

8. The stereoscopic display apparatus of claim 1, wherein said first image and said second image can be overlaid to form a stereoscopic image.

9. The stereoscopic display apparatus of claim 1, wherein said opaque plate is part of said housing.

10. The stereoscopic display apparatus of claim 1, wherein said opaque plate is a PVC plastic hardcover.

11. A stereoscopic display apparatus comprising:
    a first image displayer, for projecting a first image light;
    a second image displayer, for projecting a second image light;
    an aspherical reflection mirror, for refracting said first image light and said second image light, and for changing a polarity of a refraction light of first image light and a refraction light of second image light;

a beamsplitter, disposed within said first image displayer, said second image displayer and said aspherical reflection mirror, for deflecting a proceeding route of said refraction light of first image light and said refraction light of second image light based on said polarity of said refraction light of first image light and said refraction light of second image light; and a housing, for containing said first image displayer, said second image displayer, said aspherical reflection mirror and said beamsplitter, said housing having a first opening and at least one second opening, said refraction light of first image light and said refraction light of second image light are through said first opening thus overlaid with an image of an external object to generate a first image and a second image, said second opening used for an operator to inspect said first image and said second image through;

wherein said first image displayer and said second image displayer are used for receiving an electrical signal of a left-eye image and a right-eye image respectively, and said left-eye image is said first image and said right-eye image is said second image.

12. The stereoscopic display apparatus of claim 11, wherein said first image displayer and said second image displayer are electrically connected to an multimedia apparatus for receiving an electrical signal of said first image and said second image relative to said external object, the first image displayer and the second image displayer are used for converting said electrical signal of said first image and said second image into said first image light and said second image light.

13. The stereoscopic display apparatus of claim 12, wherein said multimedia apparatus is a computer.

14. The stereoscopic display apparatus of claim 11, wherein said aspherical reflection mirror is used for increasing the light sensitivity and distortion correction capability of said first image light and said second image light.

15. The stereoscopic display apparatus of claim 11, wherein said beamsplitter is a multilayer coating beamsplitter which can reduce the specular reflection, increase the translucence and change the polarity of a light wave.

16. The stereoscopic display apparatus of claim 11, wherein said housing contains a control module for controlling said first image displayer and said second image displayer.

17. The stereoscopic display apparatus of claim 11, further comprising an anti-glare goggles installed on said opening.

18. The stereoscopic display apparatus of claim 11, wherein said first image and said second image are overlaid to form a stereoscopic image.

* * * * *